(12) United States Patent
O'Brien et al.

(10) Patent No.: US 7,111,757 B1
(45) Date of Patent: Sep. 26, 2006

(54) DEVICE AND METHOD FOR THE VOLUMETRIC MEASUREMENT AND DISPENSING OF LIQUIDS

(76) Inventors: Thomas Matthew O'Brien, 8481 Huffman Rd., New Lebanon, OH (US) 45345; Charles William Merten, 153 Shenandoah Trail, Dayton, OH (US) 45449

( * ) Notice: Subject to any disclaimer, the term of this patent is extended or adjusted under 35 U.S.C. 154(b) by 254 days.

(21) Appl. No.: 10/660,894

(22) Filed: Sep. 12, 2003

(51) Int. Cl.
*B67D 5/16* (2006.01)

(52) U.S. Cl. ............... 222/71; 222/1; 222/63; 222/72; 222/135; 222/340; 222/386

(58) Field of Classification Search ............ 222/1, 222/71–72, 61–63, 333, 394, 52, 340, 132–135, 222/36, 386, 388–390; 422/100
See application file for complete search history.

(56) References Cited

U.S. PATENT DOCUMENTS

| | | | |
|---|---|---|---|
| 3,718,438 A | * | 2/1973 | Anscherlik ............. 422/310 |
| 3,831,618 A | | 8/1974 | Liston |
| 3,901,653 A | * | 8/1975 | Jones et al. .............. 222/71 |
| 4,189,943 A | | 2/1980 | Faure |
| 5,127,547 A | * | 7/1992 | Gerich .................. 222/55 |
| 5,277,333 A | * | 1/1994 | Shimano ................ 222/14 |
| 5,584,416 A | * | 12/1996 | Florian .................. 222/1 |
| 5,680,960 A | * | 10/1997 | Keyes et al. ............ 222/64 |
| 5,741,554 A | * | 4/1998 | Tisone .................. 427/424 |
| 5,772,899 A | * | 6/1998 | Snodgrass et al. ........ 210/767 |
| 5,862,958 A | | 1/1999 | Edwards |
| 6,036,668 A | * | 3/2000 | Mathis .................. 604/29 |

OTHER PUBLICATIONS

BrandTech Scientific, Inc., Catalog, 2002/2003, pp. 42-43, 50-51.

* cited by examiner

*Primary Examiner*—Frederick C. Nicolas

(57) ABSTRACT

Devices and methods for accurate volumetric measurement and dispensing of any liquid, regardless of that liquid's density and vapor pressure, are disclosed. This invention employs devices and methods which are used to eliminate free volume from a variable volume chamber. A desired volume of liquid can be measured accurately within the volume range of the chamber. These devices and methods are suitable for volumetric measurement and dispensing of any liquid, regardless of density or vapor pressure.

19 Claims, 10 Drawing Sheets

DEVICE AND METHOD FOR THE VOLUMETRIC MEASUREMENT AND DISPENSING OF LIQUIDS

BACKGROUND OF THE INVENTION

The present invention relates generally to a device and method for accurately measuring and dispensing a volume of a liquid by eliminating or minimizing the effects liquid density and liquid vapor pressure have on volumetric measurement. This eliminates the need to recalibrate the measuring device for use with a different liquid.

In chemistry labs and other research and industrial labs where basic chemistry methods and procedures are employed, it is frequently necessary to measure the volume of various liquids. Certain syringe and pump type devices have been used for volumetric measurement, but each has its limitations. Examples are the pipette or pipettor, the syringe pump, and the bottletop dispenser.

The pipette to which we refer is a hand operated syringe having a spring loaded plunger, a disposable tip, and a means for repeatably controlling the travel of the plunger within the cylinder such as a movable stop. The pipette is operated by: depressing the plunger to the stop; inserting the tip into the liquid to be aspirated, measured and dispensed; removing the tip from the container from which the liquid was aspirated; placing the pipette tip over the container into which the liquid is to be dispensed; and depressing the plunger, thus expelling the liquid into the container receiving the liquid. In traditional pipettes, the aspirated liquid is wholly contained in pipette tip and liquid never contacts plunger. A consequence is the existence of a gas volume between the liquid and the plunger.

Most pipettes are calibrated with distilled water at a standard temperature. When aspirating a liquid having properties which differ from water, the volume aspirated at any given stop position can differ significantly from the volume of water which would be aspirated at the same stop position. The specific liquid properties affecting accuracy are density and vapor pressure. Recalibration for the second liquid is only valid for the stop position at which the recalibration was conducted. The range of the scale indicating volume of liquid to be aspirated as a function of stop position will be different for the second liquid. Stated differently, for given minimum and maximum volumes of aspirated liquid, the distance between the minimum and maximum stop locations for the second liquid will be different than those for water. Complicating the matter of accuracy even further, the volume of liquid aspirated can be highly dependent on temperature owing to slight variations in density and much larger variations in vapor pressure.

Recently, pipette manufacturers have recognized a way to overcome the effects of density and vapor pressure on accuracy. Syringe tips for pipettes are now commercially available. The syringe tip has the appearance of common syringe, but has an elongated integral plastic tip having a diameter which is reduced with respect to the syringe body. What differentiates the syringe tip from the traditional syringe is the plunger. The plunger is designed so that when it is fully advanced, it occupies all free volume within the syringe tip as well as isolating free volume from the liquid in the transition zone between the syringe body and syringe tip. By eliminating gas from the syringe, the effects of liquid density and vapor pressure are largely negated.

The pipette with syringe tip is well suited to manual volumetric dispensing in which the user is relied upon to position the syringe tip for aspiration and dispensing of liquid. However, this concept does not work when tubing or valves are added to automate the liquid measurement and dispensing process. A solid syringe plunger tip cannot be made to penetrate a curved fluid conduit nor fill the complex internal geometry of a valve. Thus, this technology cannot be used to exclude all free volume when fluid aspiration involves the use of curved fluid conduits or valves.

Others have attempted to overcome this limitation by using a pusher fluid to occupy free volume within liquid volumetric and dispensing systems. Typically, the pusher fluid is either "immiscible" with the liquid to be aspirated or separated from the aspirated liquid by a bubble. To aspirate liquid, the pusher fluid is advanced to the orifice through which aspiration is to occur, the orifice is immersed in the liquid to be aspirated, and the pusher fluid is retracted from the orifice. Except in situations where liquid volumes and tubing diameters are extremely small, this approach does not work well. If a bubble is used to maintain separation between the aspirated liquid and the pusher fluid, the diameter of the containment for the aspirated fluid must be kept small or the bubble will collapse and the aspirated liquid and pusher fluid will commingle causing both accuracy and cross contamination problems. If the separating bubble is eliminated, the immiscible fluid will contact the aspirated liquid. When dispensing, it is difficult if not impossible to accurately detect the interface between the two different liquids so that all of the aspirated liquid but none of the pusher fluid is dispensed. In addition, cross contamination is a concern since no one pusher fluid is likely to be immiscible with all liquids which might be aspirated.

Another example of prior art is the syringe pump. The syringe pump is a syringe, the plunger of which is equipped with means such as a lead screw and stepper motor to move the plunger in a predictable and repeatable fashion. In any practical application, the syringe pump must be configured with tubing and valves to automate the liquid aspiration and expulsion processes. Upon the first aspiration of any given liquid, gas, owing to free volume within tubing and valves, will be aspirated into the syringe. As with the pipette, accurate volumetric measurement via the syringe pump depends on the elimination of gas from the system. If gas is allowed to remain in the system, the volume aspirated will depend on the density and vapor pressure of the liquid. After purging the gas, repetitive dispensing can be accomplished with acceptable accuracy. However, if aspiration of a second liquid is desired, it is necessary to purge the syringe pump of the first liquid to avoid cross contamination. The second liquid may then be aspirated, but it will again be necessary to purge gas from the system. Alternatively, one may use multiple syringe pumps, each dedicated to a single liquid, but this practice becomes expensive.

The bottletop dispenser is yet another example in which a single liquid is repetitively measured and dispensed. This device also needs to be purged of any gas prior to use to insure volumetric accuracy. The simplest way to accomplish this bleeding operation is to dispense liquid until gas is eliminated from the device. This results in waste liquid which must be either disposed of or returned to the bottle at some later time. Recognizing this limitation, a valve and conduit have been incorporated into some bottletop dispensers so that liquid can either be returned to the bottle or dispensed depending on the position of the valve. Nevertheless, the bottletop dispenser shares a major shortcoming with the syringe pump. If one desires to dispense a second liquid with the bottletop dispenser, this device must be purged of the first liquid, cleaned to avoid cross contamination, and primed with the second liquid. Thus it is more practical to devote a separate bottletop dispenser to each liquid to be dispensed, but this practice is also expensive.

The limitations associated with the devices discussed above illustrate the need for an accurate liquid volumetric measurement and dispensing device which compensates for the effects of liquid density and vapor pressure, which can measure and dispense unique dissimilar liquids in succession without the need for intermediate cleaning or bleeding operations, which can aspirate and dispense liquid through conduits and valves without a loss of accuracy, and which can easily be adapted to automated operation.

Accordingly, several objects and advantages of the present invention are:

(a) the accurate dispensing of a variety of liquids regardless of vapor pressure or density;

(b) the ability to measure and dispense dissimilar liquids in succession without the need to perform a separate operation to purge the prior liquid from the system;

(c) the ability to remove free volume from the volumetric measurement system without removing aspirated liquid from the volumetric measurement system;

(d) removal of free volume from components having complex geometry such as curved conduits and valves;

(e) its adaptability to automated operation.

Further objects and advantages of our invention will become apparent from a consideration of the drawings and ensuing description.

BRIEF SUMMARY OF THE INVENTION

Having recognized that density and vapor pressure are the physical properties of liquids responsible for variations in accurate volumetric measurement in aspiration processes, the inventors have discovered that by eliminating or minimizing free volume in aspiration systems, liquid to liquid variations in volume aspirated can be eliminated or minimized.

Aspiration devices work by creating a pressure differential between the cavity into which the liquid is to be aspirated and the pressure acting over the liquid outside the cavity. This is generally accomplished by moving a member inside the cavity. The height to which a column of liquid will rise is dependent on both the pressure differential and the density of the liquid. Syringe type devices correlate volume to liquid column height.

The effects of vapor pressure and temperature are as follows. When a liquid and gas are in contact with each other, the matter comprising the liquid is constantly vaporizing from the liquid into the gaseous phase and condensing from the gaseous phase into the liquid phase. At equilibrium, the partial pressure exerted by the gaseous phase of the matter comprising the liquid is the vapor pressure of the liquid. For most liquids, the vapor pressure varies significantly with temperature. In a syringe type device where a contained gas volume is situated over the aspirated liquid, the partial pressure exerted by the aspirated liquid in the gaseous phase will displace liquid in the syringe type device by pushing it out the open end. For liquids with high vapor pressures such as organic solvents, this effect is more pronounced than for liquids with low vapor pressures. Changes in temperature of less than 1° Celsius can produce measurable changes in the volume of liquid aspirated by a syringe type device due to changes in vapor pressure.

When gas is eliminated from syringe type aspiration devices, the pressure differential between the interior and exterior of the device remains constant and liquid will rise until it meets the plunger or cavitates. By eliminating free volume from the interior of syringe type aspiration devices, liquid must come to equilibrium with the solid surface of the plunger, eliminating or minimizing the effects of vapor pressure and hence temperature.

Elimination of free volume also obviates the need to account for free volume when determining liquid volume.

The present invention fulfills the need for an accurate syringe based volumetric measurement device: which can be used either for repetitive dispensing of the same liquid or successive dispensing of different liquids without the need to recalibrate; which can be used for successive dispensing of different liquids without bleeding the system between dispenses; which can be coupled to devices with complex internal geometries such as valves and curved conduits without affecting the accuracy of the volume of the aspirated liquid; which can easily be incorporated into an automated system. These objects are achieved by various components of the invention acting in conjunction with each other to manage the presence of liquid and gas in the system thereby eliminating or minimizing free volume.

BRIEF DESCRIPTION OF THE SEVERAL
VIEWS OF THE DRAWING

The following detailed description of the method and devices can be best understood when read while viewing the following drawings.

DETAILED DESCRIPTION OF THE INVENTION

Figure 1:
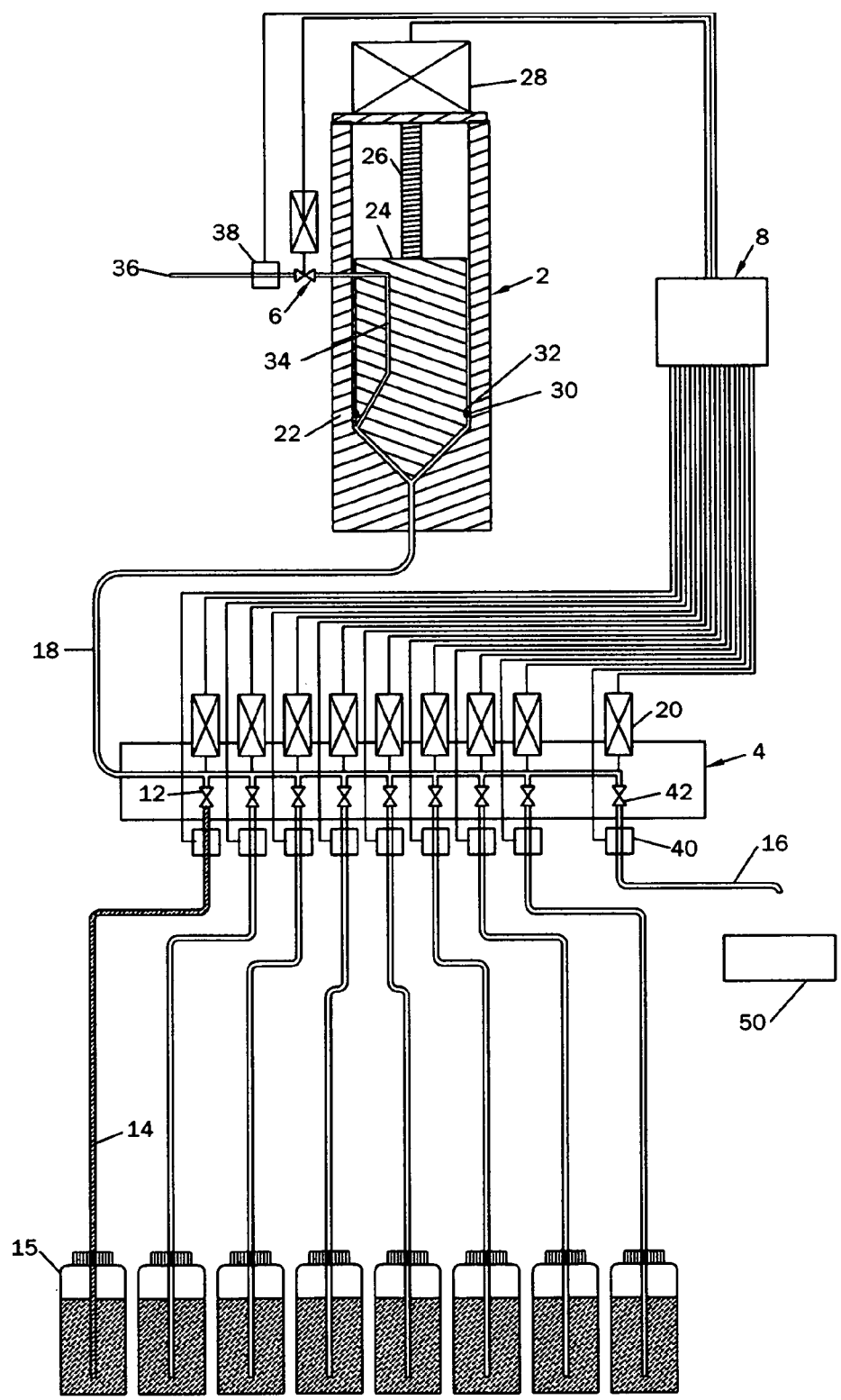
FIG. 1 is a schematic illustration of an embodiment of the present invention.

The first embodiment of this method and invention is a single pump system for measuring and dispensing single liquids and mixtures of liquids in precise, accurately measured volumes. This system, shown in FIG. 1, consists of a syringe pump 2, a valve manifold 4 (with multiple valves) and an air valve 6. The valve manifold contains valves 12 and 42, several supply lines or conduits 14, an outlet or dispensing line/nozzle or conduit 16, and a line or conduit leading to a syringe pump 18. It will become apparent that only a single supply line is required although multiple supply lines are particularly well served by this invention. The syringe pump 2 is comprised of a cylinder or cavity 22, piston or member 24, and a means to displace the piston within the cylinder such as a lead screw 26 and stepper motor 28. The piston 24 may have at least one o-ring 30 partially contained inside a groove 32 around its circumference, which seals with the cylinder 22. The piston 24 may also have two o-rings or other suitable seal for improved sealing. Displacement of the piston 24 inside the cylinder 22 changes the volume of the chamber formed by the cylinder end, wall, and piston bottom. The piston contains a hollow passage or conduit 34 which leads from the inside of the chamber to an air valve 6. The piston 24 and cylinder 22 are oriented so that the mouth of the passage 34 within the piston 24 is located at the highest practical point within the variable volume chamber, thus allowing air to escape from the chamber. The outlet of the air valve is open to the atmosphere or a body of gas 36. Air valve liquid sensing device or detector 38 is located on either side of the air valve 6. Dispense valve liquid sensing device or detector 40 is located on either side of the dispense valve. All components are connected with appropriately sized tubing.

This system is specifically designed to have a minimal internal volume when the syringe piston 24 is fully inserted into the cylinder 22. This is intended to reduce the amount of air initially present in the system. The location, size, and arrangement of the internal passages of this system are such that at one specified volume (such as 10 mL) the system can accurately measure the volume of a liquid regardless of that liquid's density or vapor pressure. This measured volume remains accurate regardless of which supply line 14 and valve 12 are used.

Figure 2:
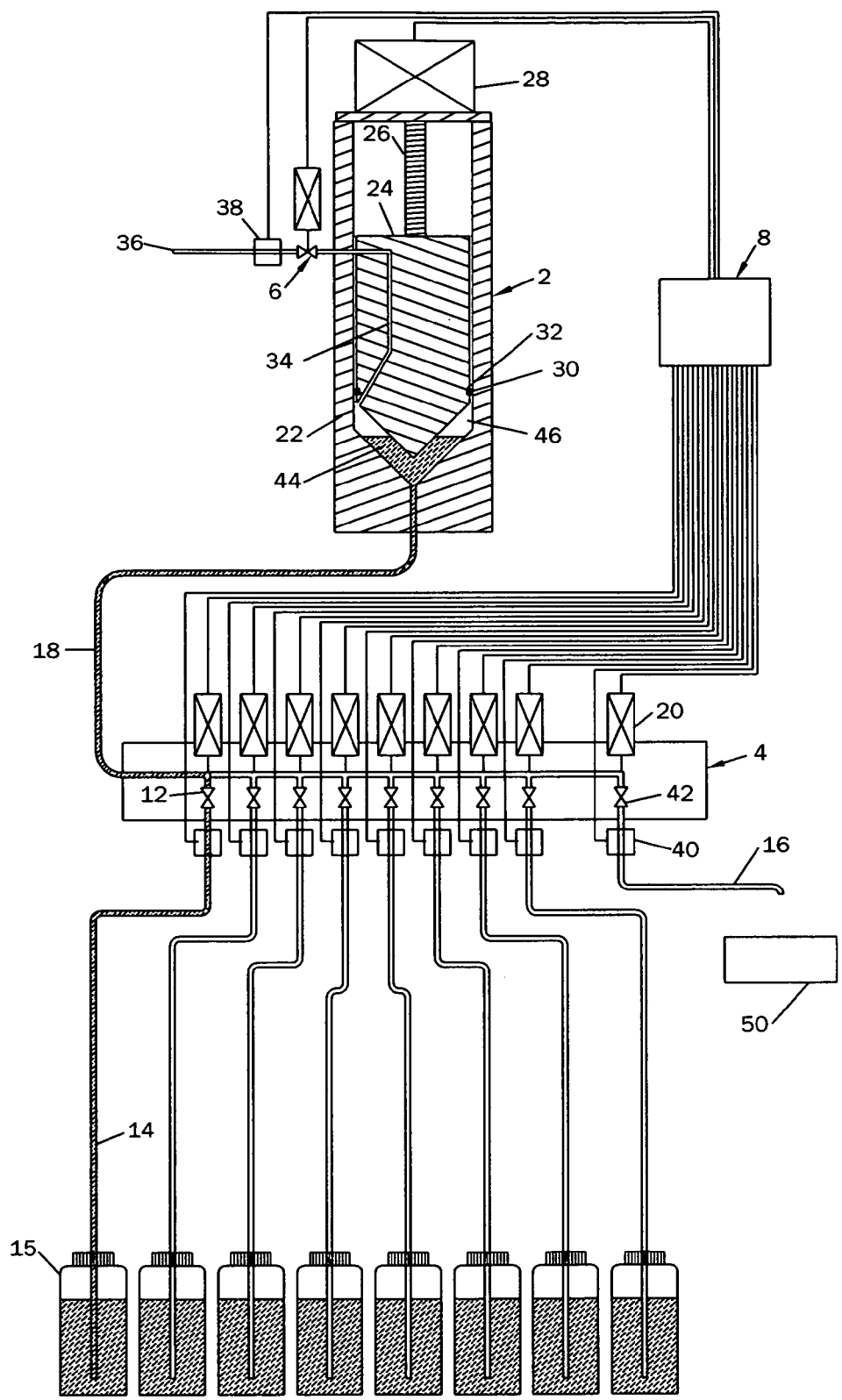
FIG. 2 is an illustration of the initial step in the volume measurement sequence conducted by the device from FIG. 1.
Figure 3:
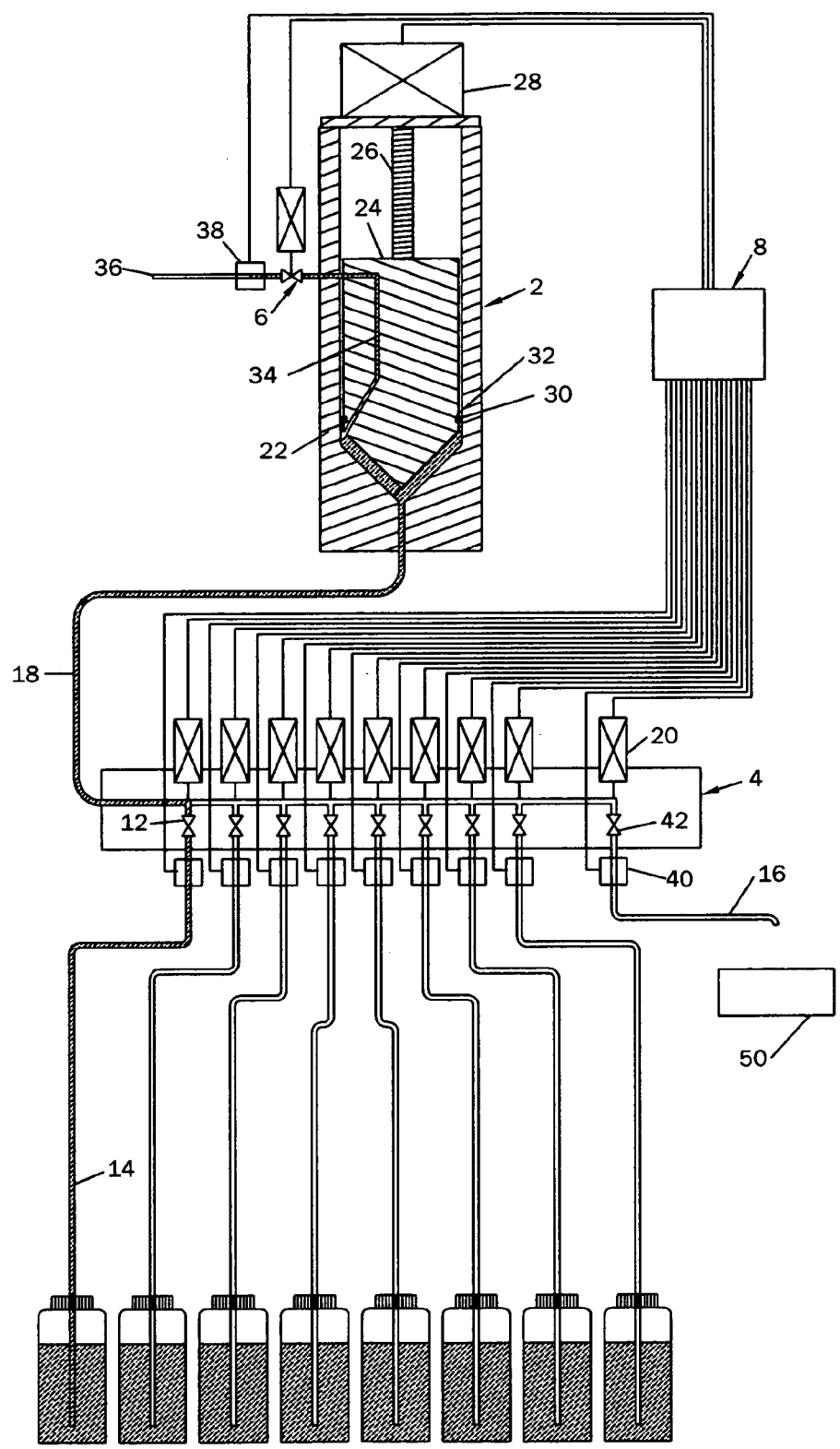
FIG. 3 is an illustration of the second step in the volume measurement sequence conducted by the device from FIG. 1.
Figure 4:
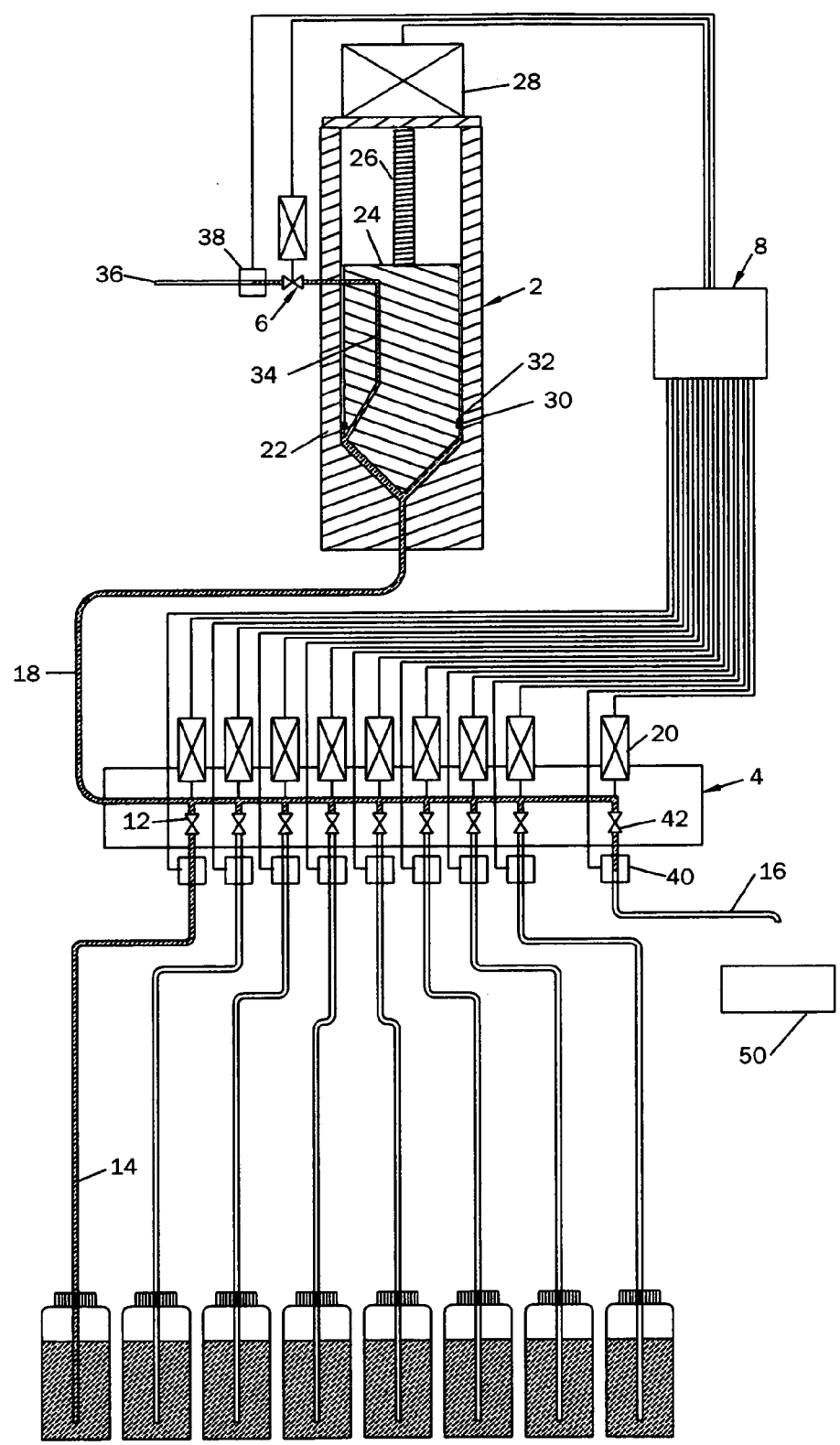
FIG. 4 is an illustration of the third step in the volume measurement sequence conducted by the device from FIG. 1.
Figure 5:
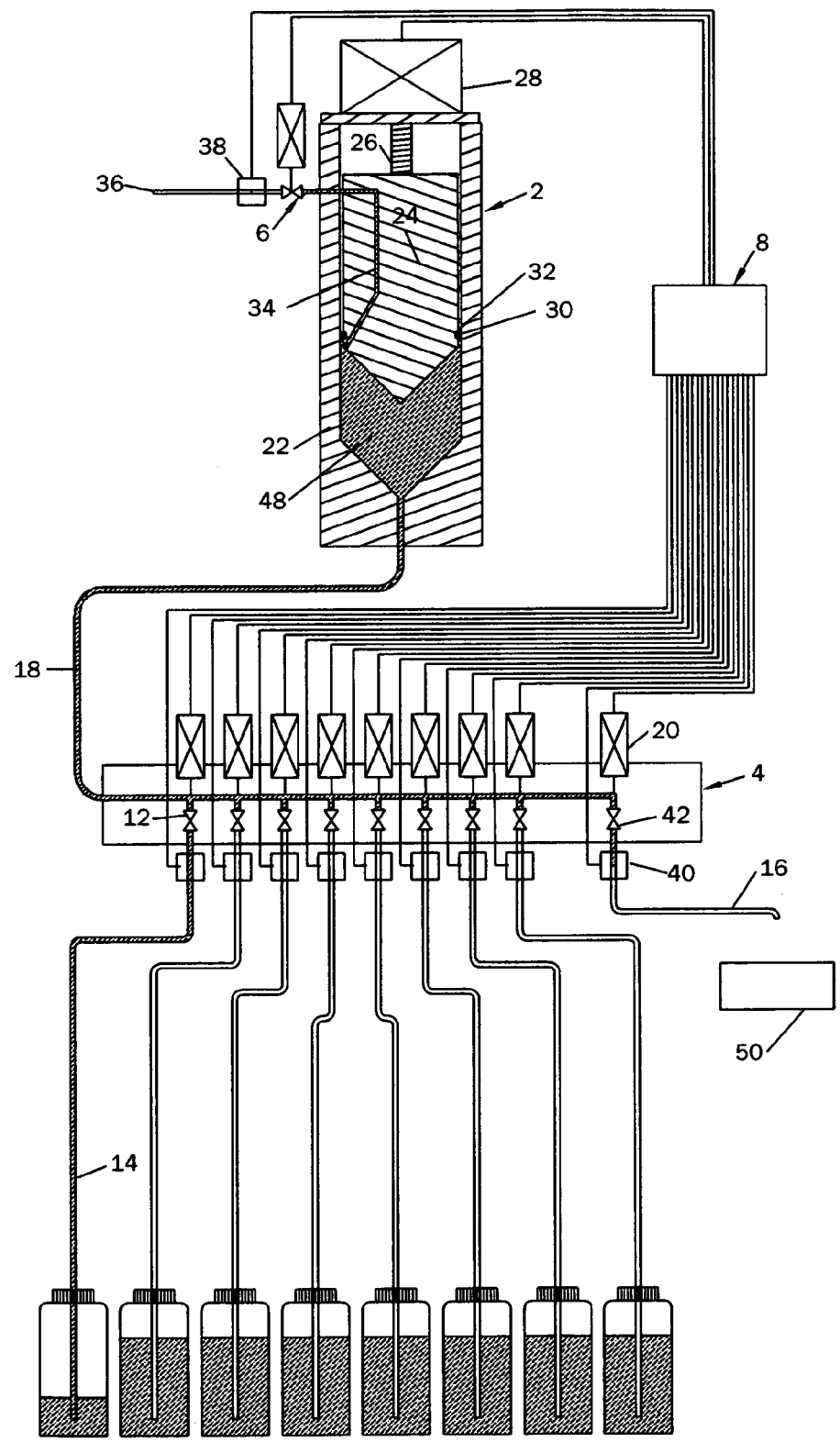
FIG. 5 is an illustration of the fourth step of the present method conducted by the device from FIG. 1.
Figure 6:
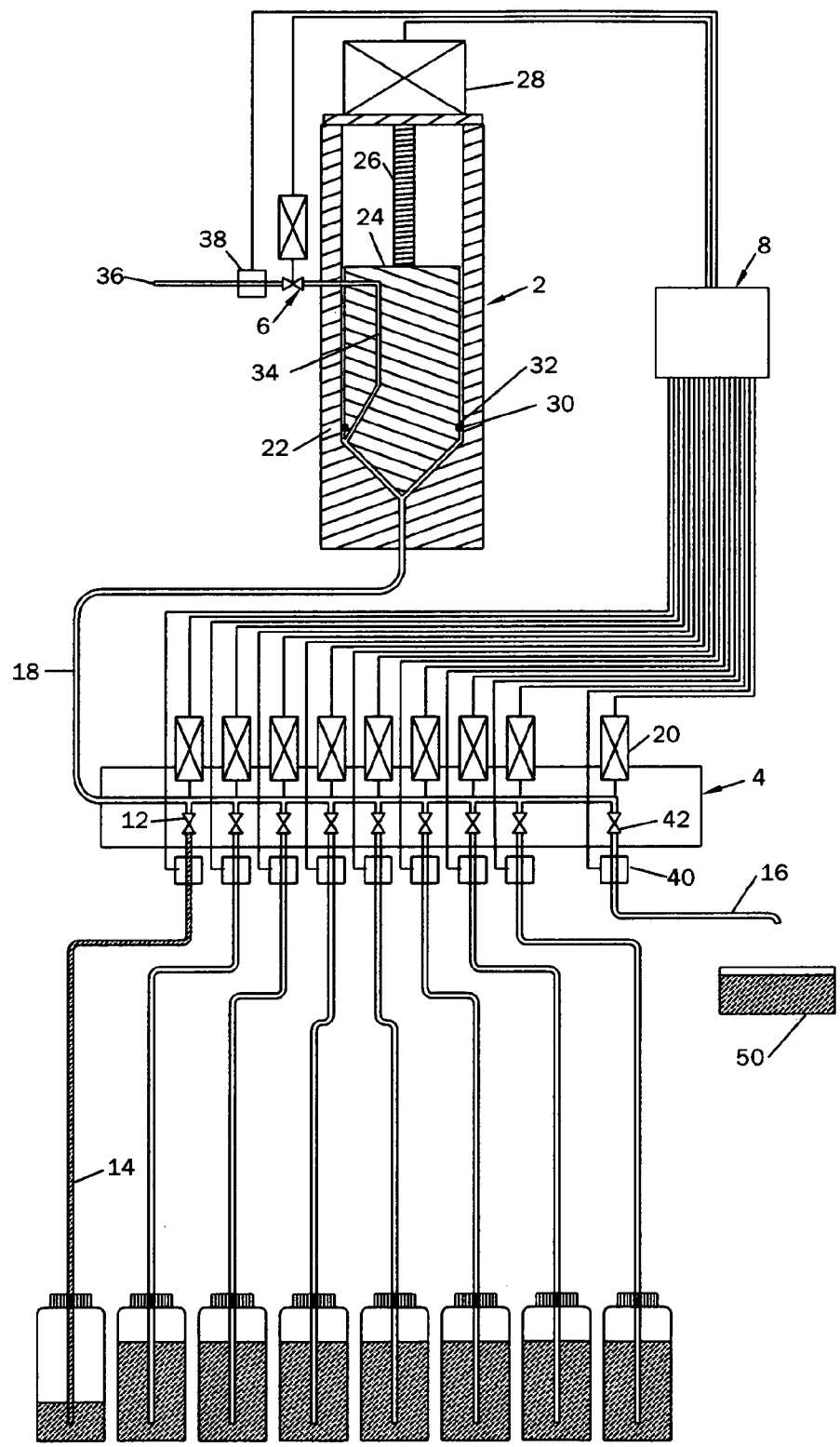
FIG. 6 is an illustration of the final step in the volume measurement sequence conducted by the device from FIG. 1.

To begin the volume measurement process, the system starts with the syringe pump piston 24 at the bottom of its stroke as shown in FIG. 1. This eliminates most of the air in the system. Next, the desired supply line valve 12 is opened and the syringe piston 24 is displaced upward (away from the bottom of the cylinder 22) a known distance, as shown in FIG. 2. This movement of the syringe draws a volume of liquid 44 into the system from a container 15 through the supply line 14. The supply line valve 12 is then closed and the air valve 6 leading from the syringe piston 24 is opened. The syringe piston 24 is then displaced downward, as shown in FIG. 3, forcing the liquid in the system through the tubing 34 leading to the air valve 6. Using a liquid sensing device 38 to sense the position of the liquid, the liquid is pushed just past the air valve 6 and the valve is closed. This procedure removes the air from inside the syringe pump 2. Next, the dispense line valve 42 is opened. The syringe piston 24 is once again displaced in the downward direction, as shown in FIG. 4, pushing the liquid just past the dispense valve 42 sensing the position of the liquid using liquid sensing device 40. The dispense valve 42 is then closed. This procedure removes the air from inside the valve manifold 4. At this point in the process there is no air in the system, only liquid. The volume of liquid is known by virtue of the position of the piston 24 in the syringe pump 2 and the known volumes of the valve manifold 4, conduits 18, and hollow passage 34. The supply line valve 12 is then opened. The syringe piston 24 is then displaced upward a known distance that will result in the intake of the desired volume of liquid 48, as shown in FIG. 5. After the piston 24 has been displaced, the system pauses to allow any cavitation to subside. The supply valve 12 is then closed. At this stage the system contains the exact desired volume of a specified liquid. This correct volume is then expelled into an appropriate container 50 by opening the dispense line valve 42 and displacing the syringe piston 24 fully downward, as shown in FIG. 6. The dispense line valve 42 is then closed and the air valve 6 is opened. The piston 24 is retracted upward fully, drawing in a full volume of air. The air valve 6 is then closed. The dispense line valve 42 is once again opened and the syringe piston 24 is displaced fully downward, expelling the remaining liquid. This purging process can be repeated as many times as necessary to expel any residual liquid thereby producing the required precision for volume measurement.

Figure 7:
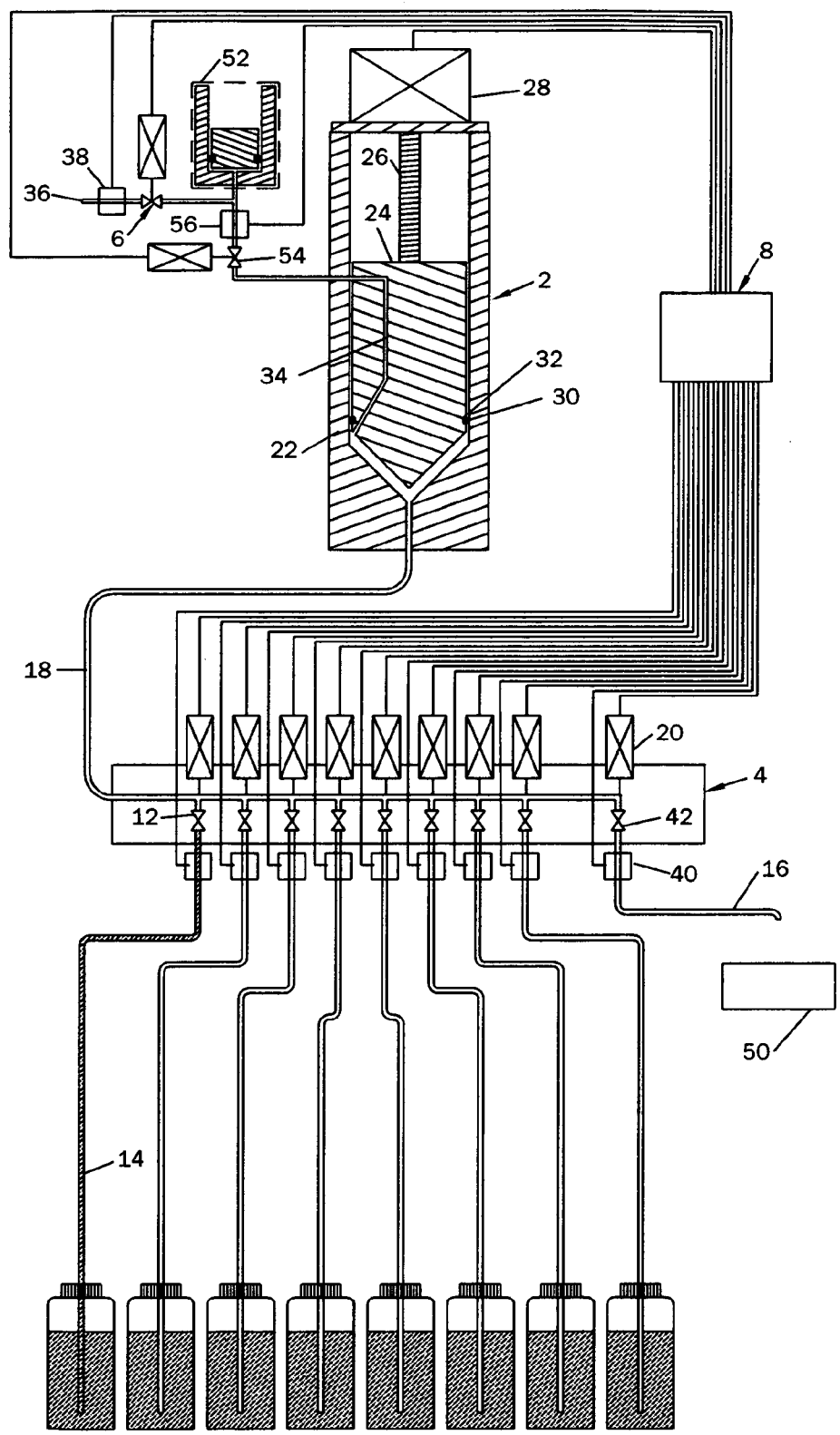
FIG. 7 is an illustration of an alternate embodiment of the device from FIG. 1, which contains a second pump.
Figure 8:
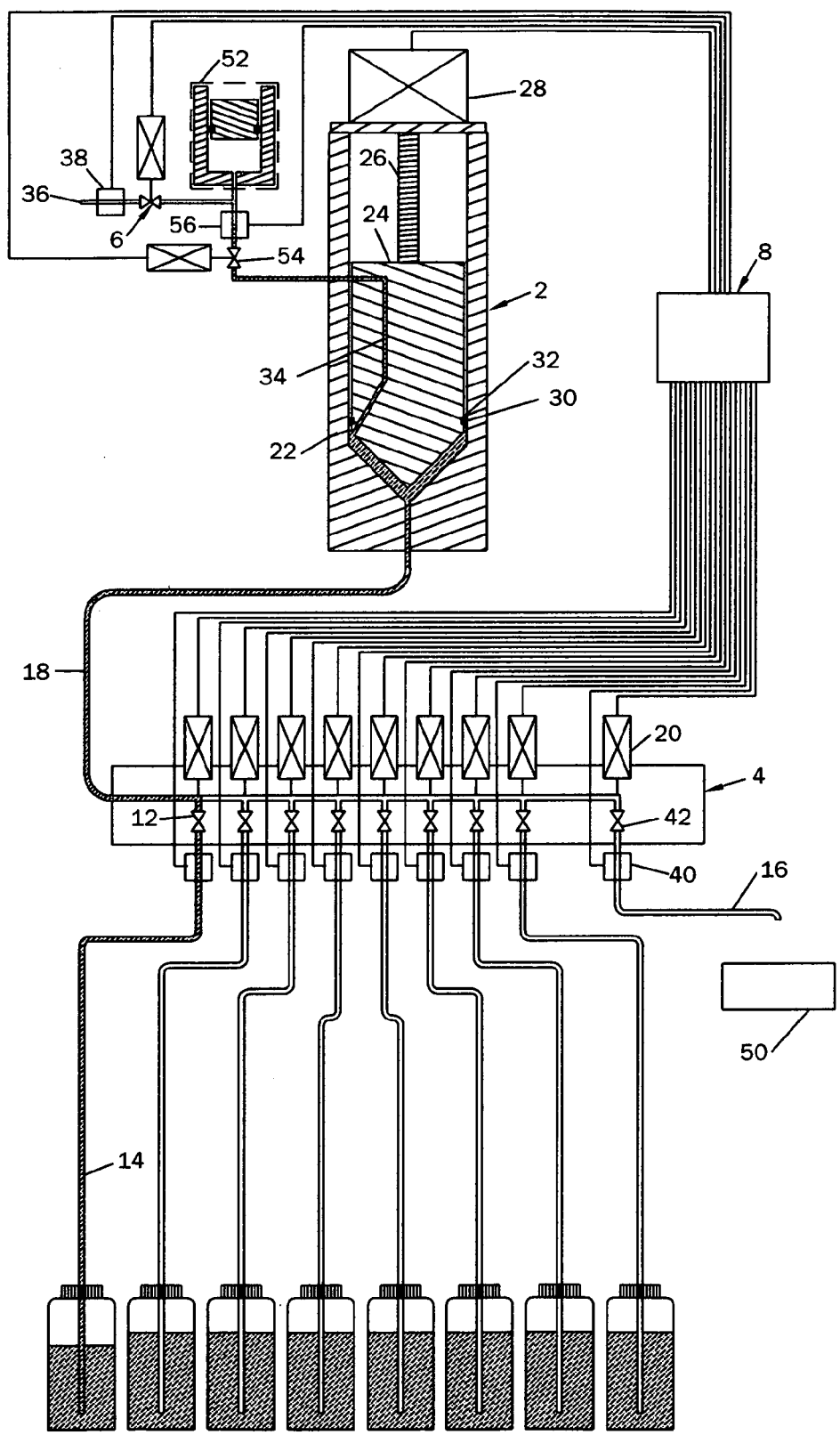
FIG. 8 is an illustration of the initial step in the volume measurement sequence conducted by the device from FIG. 7.
Figure 9:
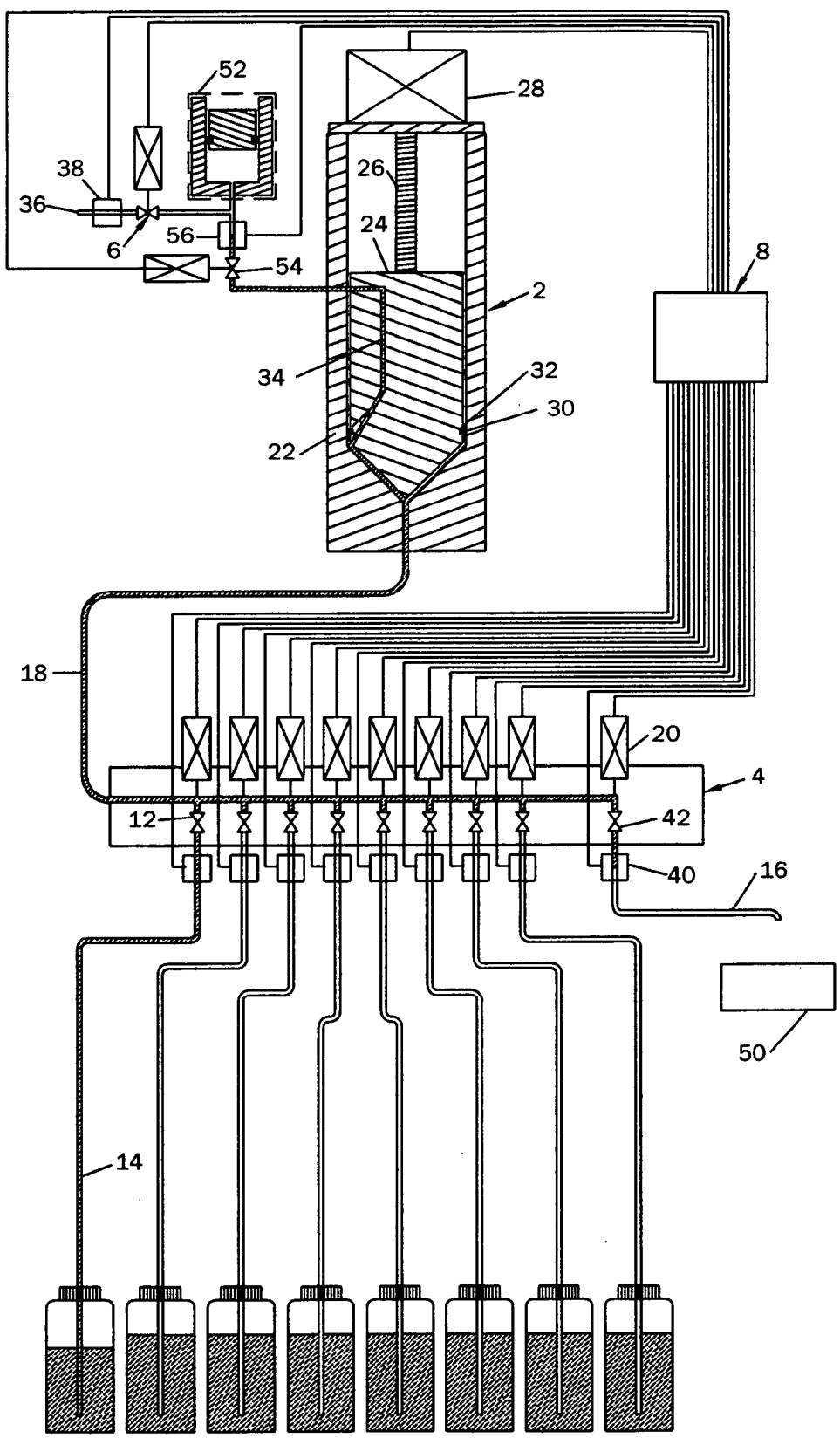
FIG. 9 is an illustration of the second step in the volume measurement sequence conducted by the device from FIG. 7.

An alternate embodiment of this device, shown in FIG. 7, is created by adding a secondary pump 52, another valve 54, and another liquid sensing device or detector 56. The initial air removal step, as shown in FIG. 8, is achieved through the use of the secondary pump 52. This is accomplished by first opening the supply valve 12, and then opening the secondary pump valve 56. The secondary pump 52 is then operated until the liquid has been detected by the secondary pump liquid sensing device or detector 56. At this point, both the supply valve 12 and secondary pump valve 54 are closed. The remaining unwanted air is removed through the use of the main syringe pump 2 as shown in FIG. 9. The dispense valve 42 is opened and the syringe pump piston 24 is displaced downward until the liquid is pushed past the dispense valve 42 and detected by the dispense valve liquid sensing device 40. From this point, the volume measurement and dispense procedure are conducted in the same manner as the previous embodiment.

Figure 10:
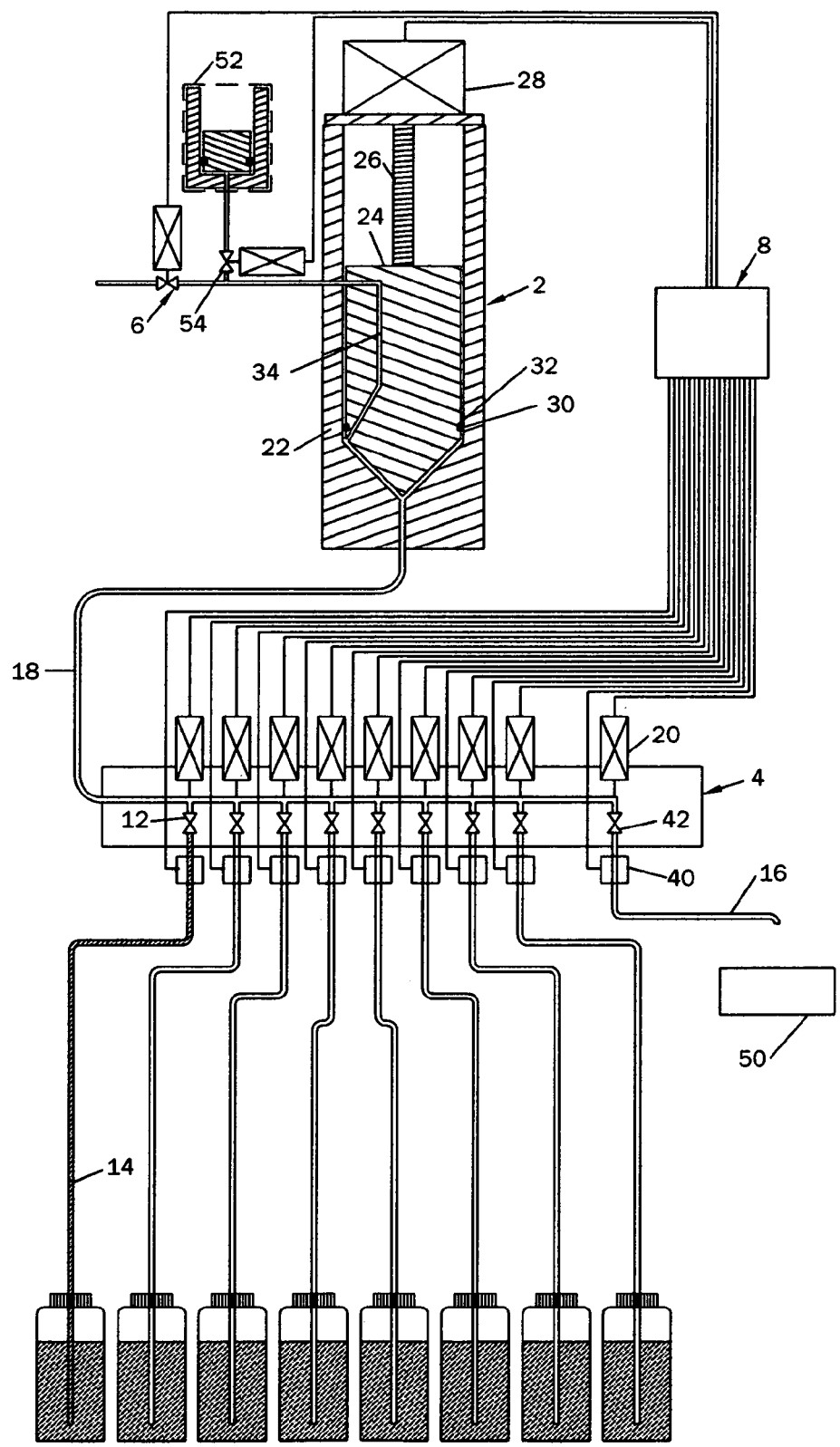
FIG. 10 is an illustration of an alternate embodiment of the device from FIG. 1 which utilizes a vacuum pump.

Another embodiment of this device is shown in FIG. 10. As with the previous embodiment, a secondary pump 52 is added to the system. The dispensing and volume measurement procedure for this device begins with the piston 24 fully inserted into the cylinder 22. Next, secondary pump valve 54 is opened while all other valves remain closed. Secondary pump 52 is then activated to remove the air from the system by creating a vacuum. Once a vacuum exists in the system, secondary pump valve 54 is then closed and secondary pump 52 is deactivated. With the system still under vacuum, supply valve 12 is opened, filling the system with liquid. From this point, the volume measurement and dispense procedure are conducted in the same manner as the first embodiment.

Those skilled in the art will appreciate that various adaptations and modifications of the just-described preferred embodiments can be configured without departing from the scope and spirit of the invention. For example, operations may be performed in a different order to achieve an identical result or the hollow passage located in the piston might be located in the cylinder wall instead. Therefore, it is to be understood that, within the scope of the appended claims, the invention may be practiced other than as specifically described herein.

What is claimed is:

1. A device for the volumetric measurement and dispensing of liquids comprising:
   a. a variable volume chamber,
   b. a means for controllably adjusting the volume of said variable volume chamber,
   c. a plurality of valves,
   d. at least one conduit disposed between said variable volume chamber and at least one of said plurality of valves,
   e. a means to detect the presence or absence of liquid in said at least one conduit so that the precise location of said liquid in relation to said plurality of valves and said variable volume chamber is determined, and f. a means for removing gas from a system formed by said variable volume chamber, said plurality of valves, and said at least one conduit, whereby said liquid aspirated into said system substantially fills said system thereby minimizing the difference between the volume of the aspirated liquid and the volume of said system.

2. The device of claim 1, wherein said device further comprises a controller, whereby said controller is in communication with said means to detect the presence or absence of said liquid in said at least one conduit, said means for controllably adjusting the volume of said variable volume chamber, and a means for actuating said plurality of valves.

3. The device of claim 1, wherein at least one of said plurality of valves is in fluid communication with both said variable volume chamber and a body of gas disposed external to the volume defined by the interior of said system, whereby said gas may be controllably expelled into said body of gas from said system or a volume of gas may be aspirated into said system from said body of gas.

4. The device of claim 3, wherein said at least one of said plurality of valves is in fluid communication with both said variable volume chamber and a container, whereby said liquid may be controllably aspirated into said variable volume chamber from said container or expelled from said variable volume chamber.

5. The device of claim 1, wherein said means for removing gas from said system formed by said variable volume chamber, said plurality of valves, and said at least one conduit further comprises a means to minimize the volume of said variable volume chamber prior to aspiration of said liquid.

6. The device of claim 1, wherein said means for removing gas from said system formed by said variable volume chamber, said plurality of valves, and said at least one conduit further comprises a means to substitute said liquid for said gas within said system by controllably adjusting the volume of said variable volume chamber in conjunction with the operation of said at least one of said plurality of valves.

7. The device of claim 1, wherein said means for removing gas from said system formed by said variable volume chamber, said plurality of valves, and said at least one conduit further comprises a means to fill said system with said liquid while maintaining a constant volume of said system.

8. The device of claim 1, wherein said means for removing gas from said system formed by said variable volume chamber, said plurality of valves, and said at least one conduit further comprises a means to controllably create a vacuum within said system, whereby said liquid aspirated into said system will completely fill said system.

9. The device of claim 1, wherein said variable volume chamber further comprises:
a. a cavity of uniform cross section with respect to the longitudinal axis of said cavity,
b. an opening at one end of said longitudinal axis of said cavity,
c. an orifice of cross sectional area equal to or less than the cross sectional area of said cavity located at the end opposite to said opening, and
d. a member slidably engaged in said cavity having a geometry substantially conforming to the geometry of said cavity, whereby said member may be retracted from said orifice of said cavity to aspirate said liquid into said cavity, and said member may be advanced toward said orifice to expel said liquid from said cavity.

10. A device for the volumetric measurement and dispensing of liquids comprising
a. a variable volume chamber,
b. a means for controllably adjusting the volume of said variable volume chamber,
c. at least one valve,
d. at least one conduit disposed between said variable volume chamber and said at least one valve for the purpose of aspirating liquid into or dispensing said liquid from said variable volume chamber, and
e. a means for removing gas from a system formed by said variable volume chamber, said at least one valve, and said at least one conduit, said means for removing gas comprising a fluid path extending from the interior to the exterior of said variable volume chamber, said fluid path being distinct from said at least one conduit, and said fluid path in fluid communication with at least one additional valve, whereby said liquid aspirated into said system substantially fills said system thereby minimizing the difference between the volume of said aspirated liquid and the volume of said system.

11. The device of claim 10, wherein said device further comprises a controller, whereby said controller is in communication with said means for controllably adjusting the volume of said variable volume chamber, a means for actuating said at least one valve, and a means for actuating said at least one additional valve.

12. The device of claim 10, wherein said at least one additional valve in fluid communication with said fluid path is in fluid communication with a body of gas disposed external to the volume defined by the interior of said system whereby said gas may be either controllably expelled into said body of gas from said system or a volume of gas may be aspirated into said system from said body of gas.

13. The device of claim 12, wherein said at least one valve is in fluid communication with a container, whereby said liquid may be controllably aspirated into said variable volume chamber from said container or expelled from said variable volume chamber.

14. The device of claim 10, wherein said means for removing gas from said system formed by said variable volume chamber, said at least one valve, and said at least one conduit further comprises a means to minimize the volume of said system.

15. The device of claim 10, wherein said means for removing gas from said system formed by said variable volume chamber, said at least one valve, and said at least one conduit further comprises a means to fill said system with said liquid by controllably adjusting the volume of said variable volume chamber in conjunction with the operation of said at least one additional valve in fluid communication with said fluid path.

16. The device of claim 10, wherein said means for removing said gas from said system formed by said variable volume chamber, said at least one valve, and said at least one conduit further comprises a means to fill within said system with said liquid while maintaining a constant volume of said system.

17. The device of claim 10, wherein said means for removing gas from said system formed by said variable volume chamber, said at least one valve, and said at least one conduit further comprises a means to controllably create a vacuum within said system, whereby said liquid aspirated into said system will completely fill said system.

18. The device of claim 10, wherein said variable volume chamber further comprises:
   a. a cavity of uniform cross section with respect to the longitudinal axis of said cavity,
   b. an opening at one end of said longitudinal axis of said cavity,
   c. an orifice of cross sectional area equal to or less than the cross sectional area of said cavity located at the end opposite to said opening, and
   d. a member slidably engaged in said cavity having a geometry substantially conforming to the geometry of said cavity,
      whereby said member may be retracted from said orifice of said cavity to aspirate said liquid into said cavity, and said member may be advanced toward said orifice to expel said liquid from said cavity.

19. A method to accurately aspirate any given volume of liquid comprising the steps of:
   a. providing a variable volume chamber in fluid communication with at least one valve, providing at least one conduit disposed between said variable volume chamber and said at least one valve, providing a fluid path distinct from said at least one conduit, said fluid path extending from the interior to the exterior of said variable volume chamber and said fluid path being in fluid communication with at least one additional valve, and providing at least one means for detecting the presence or absence of said liquid in said fluid path,
   b. opening said at least one valve,
   c. closing said at least one additional valve,
   d. placing said at least one valve in fluid communication with said liquid to be aspirated,
   e. aspirating an initial volume of said liquid less than said given volume of said liquid into a system formed by said variable volume chamber, said at least one conduit, and said fluid path, by controllably increasing the volume of said variable volume chamber,
   f. closing said at least one valve,
   g. opening said at least one additional valve,
   h. exhausting gas from said system through said fluid path by controllably decreasing the volume of said variable volume chamber until said liquid is displaced to a precise location in said fluid path predetermined by the position for said at least one means of detecting the presence or absence of said liquid,
   i. closing said at least one additional valve,
   j. opening said at least one valve,
   k. aspirating an additional volume of said liquid equal to the difference in volume between said given volume of said liquid and said initial volume of said liquid,
      whereby said given volume of said system in conjunction with said exhausting gas from said system results in an accurate measurement of the volume of said liquid.

* * * * *